United States Patent [19]

Miyajima et al.

[11] Patent Number: 5,422,360
[45] Date of Patent: Jun. 6, 1995

[54] MAILLARD REACTION INHIBITOR

[75] Inventors: Keisuke Miyajima, Shiga; Bonpei Yasui, Nara; Masaaki Motoyama, Shiga; Shintaro Ishikawa, Kyoto; Koichi Yasumura, Shiga, all of Japan

[73] Assignee: Otsuka Pharmaceutical Co., Ltd., Tokyo, Japan

[21] Appl. No.: 95,994

[22] Filed: Jul. 23, 1993

Related U.S. Application Data

[62] Division of Ser. No. 933,692, Aug. 24, 1992, abandoned.

[30] Foreign Application Priority Data

Aug. 27, 1991 [JP] Japan .................................. 3-215621

[51] Int. Cl.$^6$ .................. C05D 233/96; C07D 233/70; A61K 31/415
[52] U.S. Cl. ................................. 514/391; 514/390; 548/184; 548/321.5
[58] Field of Search ........................... 548/321.5, 184; 514/390, 391

[56] References Cited

U.S. PATENT DOCUMENTS

| 2,739,971 | 3/1956 | Sawdey et al. |
|---|---|---|
| 3,641,019 | 2/1972 | Trepanier et al. |
| 3,704,296 | 11/1972 | Mousseron ............................ 548/183 |
| 4,402,964 | 9/1983 | Rasmussen . |
| 4,657,922 | 4/1987 | Rasmussen et al. |
| 4,758,583 | 7/1988 | Cerami et al. |
| 4,908,446 | 3/1990 | Ulrich et al. |

FOREIGN PATENT DOCUMENTS

| 443988 | 1/1972 | Australia . |
|---|---|---|
| 932674 | 9/1955 | Germany . |
| 936688 | 12/1955 | Germany . |
| 1038050 | 11/1956 | Germany . |
| 2405395 | 8/1974 | Germany . |
| 0185346 | 12/1985 | Germany . |
| 0373542 | 12/1989 | Germany . |
| 0381628 | 1/1990 | Germany . |
| 64-56614 | 8/1987 | Japan . |
| 64-83059 | 9/1987 | Japan . |
| 2109792 | 6/1983 | United Kingdom . |
| 0132914 | 4/1984 | United Kingdom . |
| 2134513 | 8/1984 | United Kingdom . |

OTHER PUBLICATIONS

C.A. 89 (43345.w) 1978, Svetkin et al.
Hideaki, Yakugaku Zasshi 87(2) 142–147 (1967).
Kapustyak, Farm. Zhor. 1959 6. Abstract only.
Tamayo, Bull Chem Soc. 1964 p. 255.
Kikkawa et al. *Diabetologia,* 24:290–292 (1983).
Soulis-Liparota et al, *Diabetes, 40: 1328–34 (1991).*
Svetkin et al, Heterocycles, 77: 139872u (1972). (with copy of original publication).
Minlibaeva et al, Chemical Abstracts, 88: 190664g (1978).
Hassan et al, Chemical Abstracts, 110: 135199g (1989).
Turkevich et al, Chemical Abstracts, 74: 13100k (1971). (with copy of original publication).

*Primary Examiner*—Robert Gerstl
*Attorney, Agent, or Firm*—Sughrue, Mion, Zinn, Macpeak & Seas

[57] ABSTRACT

A novel Maillard reaction inhibitor containing at least one compound represented by formula (1) and the salts thereof; methods for producing the compounds of formula (1) and the salts thereof; a composition for inhibiting the Maillard reaction in living body comprising at least one compound of formula (1) and the salts thereof; and a method for inhibiting the Maillard reaction in living body by administration of a compound of formula (1') or a salt thereof are disclosed.

6 Claims, 1 Drawing Sheet

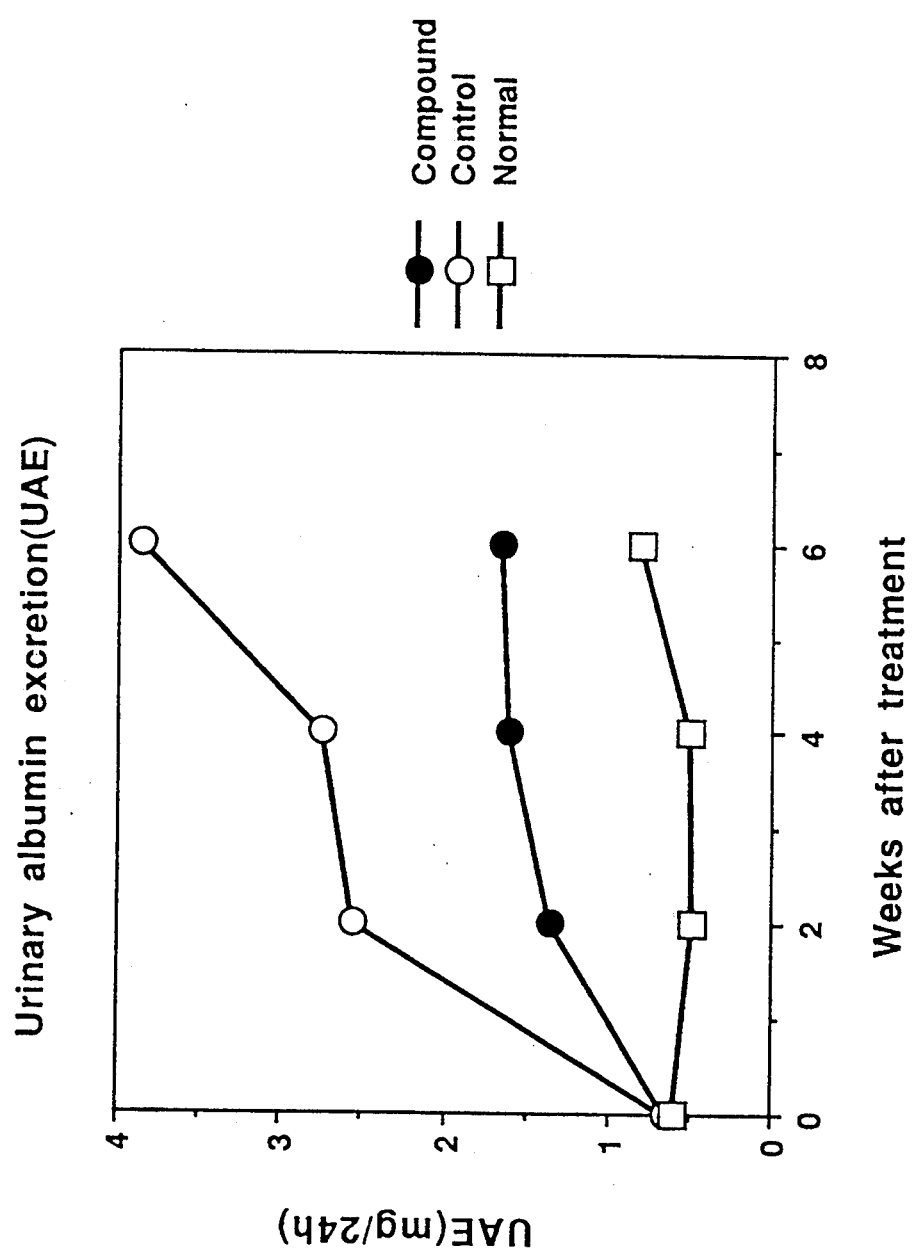
FIGURE

MAILLARD REACTION INHIBITOR

This is a Divisional of Application Ser. No. 07/933,692, filed Aug. 24, 1992, now abandoned.

FIELD OF THE INVENTION

The present invention relates to a novel Maillard reaction inhibitor.

BACKGROUND OF THE INVENTION

The Maillard reaction is a reaction which starts in a living body with an attack by a nucleophilic reaction with a free amino group present in a protein on an aldehyde group of a reducing sugar such as glucose to form a Schiff base which is called aldimine. Then, aldimine successively causes a rearrangement to form a more stable Amadori compound (non-enzymatic glycation). The Amadori compound further causes a series of reaction with other proteinous amino groups, thereby to form a brown fluorescent material and to cause a crosslinking between proteins. Historically, Maillard reported in 1912 that a mixed solution of an amino acid and a reducing sugar, when heated, is colored into brown (L. C. Maillard, Compt. Rend. Soc. Biol., 72, 599 (1912)) and, since then the reaction is called Maillard reaction. At that time, Maillard already suggested that the reaction could occur in a living body.

In 1968, Rabber et al found that hemoglobin $A_{1C}$ which is a very small fraction of hemoglobin is increased in the blood of diabetic patients (S. Rabber et al., Clin. Chim. Acta., 22, 296 (1968)] and further, it was found that the hemoglobin $A_{1C}$ was formed by bonding glucose to the N terminal valine of the hemoglobin β-chain in the form of an Anadori rearrangement (V. J. Stevens, H. Vlassara, A Abati & A. Cerami, J. Biol. Chem., 252, 2998 (1977)), etc., and the occurrence of a non-enzymatic glycation in a living body was proved.

Recently, it has been confirmed that various bioproteins may undergo the Millard reaction. For example, it is reported that the amount of hemoglobin subjected to a glycation is increased thrice in a diabetic [E. C. Abraham et al, J. Lab. Clin. Med., 102, 187 (1983)].

Also, it is reported that the amount of glycation is increased in the serum albumin of diabetic patients (R. Dolhofer and O. H. Wieland, Diabetes, 29, 417 (1980)). Also, it is reported that fluorescence is increased in the skin collagen obtained from diabetic patients (Vincent M. Monnier et al, Proc. Natl. Acad. Sci. U.S.A., 81, 583 (1984)).

The non-enzymatic glycation is a phenomenon observed in a healthy person, but the accumulation of the brown fluorescent material is a protein having a delayed metabolic turnover rate and is markedly observed in aging and a diabetic state of increasing a blood sugar value. The reason therefor has been reported by Patrick et al that an accumulated amount of the Maillard reaction product is determined by a blood sugar value, the metabolic turnover rate of the target protein thereof, etc. (J. S. Patrick, S. R. Thorpe and J. W. Baynes, Journal of Gerontology, 45, 1, B18-23 (1990)).

The correlation between such a Maillard reaction product and various cause of diseases relating to diabetes and aging has been discussed. For example, it is reported that, when a serum protein which has been subjected to glycation is intravenously administered to mice for 12 weeks, a typical renal disorder in diabetes is caused (B. A. McVerry et al, The Lancet, 5, 738 (1980)).

It is also considered that the non-enzymatic glycation of a nervous myelin protein takes part in one of the causes of the diabetic nervous disorder (V. M. Monnier et al, Clin. Endocrinol. Metab., 11, 431 (1982)).

An eyeball lens crystalline is a specific protein causing no metabolic turnover after being biosynthesized, and Cerami et al found that, when the crystalline undergoes the glycation, a colorless crosslinked compound having a disulfide linkage and a colored crosslinked compound having a fluorescence are formed (V. M. Monnier & A. Cerami, Science, 211, 491 (1981) and V. M. Monnier & A. Cerami, Biochim. Biophys. Acta., 760, 97 (1983)). When the crystalline undergoes glycation, polymerization, insolubilization, increase in fluorescence, and coloring in brown occur, closely similar to the change of the eyeball lens with aging (S. H. Chiou et al, J. Biol. Chem., 256, 5176 (1981)).

Collagen and elastin which are proteins constituting connective tissues are proteins showing very slow metabolic turnover and a combined product with glucose has been found in a renal glomerules base membrane, a skin, a tendon, etc. (V. M. Monnier et al, "Maillard Reaction in Food", Prog. Food Nutr. Sci., 5, 315, Pergamon Press, London). Brownlee et al showed that, in a diabetic rat, crosslinking of collagen increases in the wall of the blood vessel, thereby to accumulate a fluorescent material, and also that such a crosslinking occurs by a non-enzymatic mechanism (M. Brownlee et al., Science, 232, 1629 (1989)). The relation with hardening of the arterial wall has been also considered (H. Rosenburn et al, Biochem. Biophys., Res. Commun., 91, 498 (1979)).

As described above, it is considered that the Maillard reaction in a living body takes part in various diseases relating to diabetes and aging.

SUMMARY OF THE INVENTION

An object of the present invention is to provide a novel Maillard reaction inhibitor.

Another object of the present invention is to provide methods for producing the compounds of formula (1) and the salts thereof.

A still another object of the present invention is to provide a composition for inhibiting the Maillard reaction in living body comprising at least one compound of formula (1) and the salts thereof.

A further object of the present invention is to provide a method for inhibiting the Maillard reaction in living body by administration of a compound of formula (1') or a salt thereof.

That is, according to the present invention, there is provided a Maillard reaction inhibitor containing, as an active ingredient, at least one compound represented by the following formula (1') or a salt thereof;

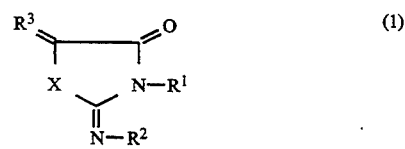

wherein $R^1$ represents a hydrogen atom, a lower alkyl group, a carboxy lower alkyl group, a lower alkoxycarbonyl lower alkyl group, a phenoxy lower alkanoyl group which may have a lower alkoxycarbonyl group on the phenyl ring thereof, or a lower cycloalkyl group; $R^2$ represents —NHR$^4$ (wherein R$^4$ represents hydrogen atom, a phenylsulfonyl group which may have from 1 to 3 substituents selected from a halogen atom, a nitro group, a lower alkoxy group and a lower alkyl group on the phenyl ring thereof, a phenyl lower alkanoyl group, or —CO—NHR$^5$ (wherein R$^5$ represents a lower alkyl group, a phenyl group which may have a halogen atom on the phenyl ring thereof, a phenyl lower alkyl group, or a naphthyl group)), or —N=R$^6$ (wherein R$^6$ represents a lower alkylidene group, a lower alkylidene group having 1 or 2 lower cycloalkyl groups, a phenyl lower alkylidene group which may have from 1 to 3 substituents selected from a halogen atom, a carboxy group, a lower alkoxycarbonyl group, a nitro group, a hydroxy group, a lower alkoxy group and a halogenated lower alkyl group on the phenyl ring thereof, a phenyl lower alkenylidene group which may have a nitro group on the phenyl ring thereof, a lower alkenylidene group, a lower cycloalkylidene group, or a phenoxy lower alkylidene group which may have a carboxy group on the phenyl ring thereof); R$^3$ represents two hydrogen atoms, a phenyl lower alkylidene group which may have a halogen atom or a halogenated lower alkyl group on the phenyl ring thereof, or a phenyl lower alkenylidene group; and X represents —S— or —N(R$^7$)— (wherein R$^7$ represents a hydrogen atom, a lower alkyl group, a carboxy lower alkyl group, or a lower alkoxycarbonyl lower alkyl group; and R$^1$ and R$^4$, or R$^4$ and R$^7$ may combine with each other to form an oxoethylene group.

The compound of formula (1') and the salt thereof according to the present invention are useful for the treatment and/or the prevention of various diabetes complications such as coronary disease, a periphery circulatory disorder, a cerebrovascular disorder, diabetic neurosis, a renal disease, an arterosclerosis, an articular sclerosis, a cataract, and retinitis or the diseases caused by aging, such as an atherosclerosis, a senile cataract, etc., by inhibiting the Maillard reaction.

BRIEF DESCRIPTION OF THE DRAWINGS

Figure is a graph showing the results on the urimary albumin excretion (mg/24 hours) for a test period of six weeks obtained according to Pharmacological Test 2.

DETAILED DESCRIPTION OF THE INVENTION

Each group used in the present invention is described hereinafter in detail.

Example of lower alkyl group, regardless of whether it exists independently or exists in other groups, include straight chain or branched alkyl groups having from 1 to 6 carbon atoms, such as methyl, ethyl, propyl, isopropyl, butyl, tert-butyl, pentyl, hexyl, etc.

Examples of the alkoxy group, regardless of whether it exists independently or exists in other groups, include straight chain or branched alkoxy groups having from 1 to 6 carbon atoms, such as methoxy, ethoxy, propoxy, isopropoxy, butoxy, tert-butoxy, pentyloxy, hexyloxy, etc.

The halogen atom, regardless of whether it exists independently or exists in other groups, means for example, fluorine, chlorine, bromine, and iodine.

Examples of the carboxy lower alkyl group include carboxyalkyl groups in which the alkyl moiety is a straight chain or branched alkyl group having from 1 to 6 carbon atoms, such as carboxymethyl, 2-carboxyethyl, 1-carboxyethyl, 3-carboxypropyl, 4-carboxybutyl, 1,1-dimethyl-2-carboxyethyl, 5-carboxypentyl, 6-carboxyhexyl, 2-methyl-3-carboxypropyl, etc.

Examples of the lower alkoxycarbonyl lower alkyl group include alkoxycarbonylalkyl groups in which the alkoxy moiety has from 1 to 6 carbon atoms and the alkyl moiety has from 1 to 6 carbon atoms, such as methoxycarbonylmethyl, ethoxycarbonylmethyl, 3-methoxycarbonylpropyl, 4-ethoxycarbonylbutyl, 6-propoxycarbonylhexyl, 5-isopropoxycarbonylpentyl, 1,1-dimethyl-2-butoxycarbonylethyl, 2-methyl-3-tert-butoxycarbonylpropyl, 2-pentyloxycarbonylethyl, hexyloxycarbonylmethyl, etc.

Examples of the phenoxy lower alkanoyl group include phenoxyalkanoyl groups in which the alkanoyl moiety is a straight chain or branched alkanoyl group having from 2 to 6 carbon atoms, such as 2-phenoxyacetyl, 3-phenoxypropionyl, 4-phenoxybutyryl, 2-phenoxybutyryl, 6-phenoxyhexanoyl, 2-phenoxypropionyl, 3-phenoxybutyryl, 4-phenoxy-3-methylbutyryl, 5-phenoxypentanoyl, 2-methyl-3-phenoxypropionyl, etc.

Examples of the phenoxy lower alkanoyl group having a lower alkoxycarbonyl group on the phenyl ring thereof include straight chain or branched alkanoyl groups of from 2 to 7 carbon atoms which have a phenoxy group having, as a substituent, a straight chain or branched alkoxycarbonyl group (wherein the alkoxy moiety has from 1 to 6 carbon atoms) on the phenyl ring thereof, such as 2-(4-methoxycarbonylphenoxy)acetyl, 2-(3,4-dimethoxycarbonylphenoxy)acetyl, 2-(3,4,5-trimethoxycarbonylphenoxy)acetyl, 2-(3-methoxycarbonylphenoxy)acetyl, 2-(2-methoxycarbonylphenoxy)acetyl, 3-(2-propoxycarbonylphenoxy)propionyl, 4-(4-pentyloxycarbonylphenoxy)butyryl, 5-(3-propoxycarbonylphenoxy)pentanoyl, 6-(4-isobutoxycarbonylphenoxy)hexanoyl, 2-(4-hexyloxycarbonylphenoxy)acetyl, 2-(4-butoxyphenoxy)acetyl, etc.

Examples of the lower cycloalkyl group include lower cycloalkyl groups having from 3 to 8 carbon atoms, such as cyclopropyl, cyclobutyl, cyclopentyl, cyclohexyl, cycloheptyl, cyclooctyl, etc.

Examples of the phenyl lower alkanoyl group include phenylalkanoyl groups in which the alkanoyl moiety is a straight chain or branched alkanoyl group having from 2 to 6 carbon atoms, such as phenylacetyl, 3-phenylpropionyl, 4-phenylbutyryl, 2,2-dimethyl-3-phenylpropionyl, 5-phenylpentanoyl, 6-phenylhexanoyl, 2-methyl-3-phenylpropionyl, etc.

Examples of the phenylsulfonyl group which may have from 1 to 3 substituents selected from a halogen atom, a nitro group, a lower alkoxy group and a lower alkyl group on the phenyl ring thereof include phenylsulfonyl groups which may have from 1 to 3 substituents selected from a halogen atom, a nitro group, a straight chain or branched alkoxy group having from 1 to 6 carbon atoms, and a straight chain or branched alkyl group having from 1 to 6 carbon atoms on the phenyl group thereof, such as phenylsulfonyl, 2-chlorophenylsulfonyl, 3-chlorophenylsulfonyl, 4-chlorophenylsulfonyl, 2-fluorophenylsulfonyl, 3-fluorophenylsulfonyl, 4-fluorophenylsulfonyl, 2-bromophenylsulfonyl, 3-bromophenylsulfonyl, 4-bromophenylsulfonyl, 2-iodophenylsulfonyl, 4-iodophenylsulfonyl, 3,5-dichlorophenylsulfonyl, 2,6-dichlorophenylsulfonyl, 3,4-dichlorophenylsulfonyl, 3,4-difluorophenylsulfonyl, 3,5-dibromophenylsulfonyl, 3,4,5-trichlorophenylsulfonyl, 2-methylphenylsulfonyl, 3-methylphenylsulfonyl, 4-methylphenylsulfonyl, 2- ethylphenylsulfonyl, 3-ethylphenylsulfonyl, 4-ethylphenylsulfonyl, 3-isopropylphenylsufonyl, 4-hexylphenylsulfonyl, 3,4-dimethylphenylsulfonyl, 2,5-dimethylphenylsulfonyl, 3,4,5-trimethylphenylsulfonyl, 2-methoxyphenylsulfonyl, 3-methoxyphenylsulfonyl, 4-methoxyphenylsulfonyl, 2-ethoxyphenylsulfonyl, 3-ethoxyphenylsulfonyl, 4-ethoxyphenylsulfonyl, 4-isopropoxyphenylsulfonyl, 4-hexyloxyphenylsulfonyl, 3,4-dimethoxyphenylsulfonyl, 3,4-diethoxyphenylsulfonyl, 3,4,5-trimethoxyphenylsulfonyl, 2,5-dimethoxyphenylsulfonyl, 2-nitrophenylsulfonyl, 3-nitrophenylsulfonyl, 4-nitrophenylsulfonyl, 2,4-dinitrophenylsulfonyl, 3-methyl-4-chlorophenylsulfonyl, 2-chloro-6-methylphenylsulfonyl, 2-methoxy-3-chlorophenylsulfonyl, etc.

Examples of the phenyl group which may have, as a substituent, a halogen atom on the phenyl ring thereof include phenyl groups which may have from 1 to 3 halogen atoms, such as phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, etc.

Examples of the phenyl lower alkyl group include phenylalkyl groups in which the alkyl moiety is a straight chain or branched alkyl group having from 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, etc.

Examples of the lower alkylidene group include straight chain or branched alkylidene groups having from 1 to 6 carbon atoms, such as methylene, ethylidene, propylidene, isopropylidene, butylidene, tert-butylidene, pentylidene, hexylidene, etc.

Examples of the lower alkylidene group having 1 or 2 lower cycloalkyl groups include straight chain or branched alkylidene groups having from 1 to 6 carbon atoms containing 1 or 2 cycloalkyl groups having from 3 to 8 carbon atoms, such as 2-cyclopropylethylidene, 1-cyclobutylethylidene, 3-cyclopentylpropylidene, 4-cyclohexylbutylidene, 1,1-dimethyl-2-cycloheptylethylidene, 5-cyclooctylpentylidene, 6-cyclohexylhexylidene, 2-methyl-3-cyclohexylpropylidene, dicyclopropylmethylene, 2-dicyclopropylethylidene, etc.

Examples of the phenyl lower alkylidene group include phenylalkylidene groups in which the alkylidene moiety is a straight chain or branched alkylidene group having from 1 to 6 carbon atoms, such as benzylidene, 2-phenylethylidene, 1-phenylethylidene, 3-phenylpropylidene, 4-phenylbutylidene, 1,1-dimethyl-2-phenylethylidene, 5-phenylpentylidene, 6-phenylhexylidene, 2-methyl-3-phenylpropylidene, etc.

Examples of the phenyl lower alkylidene group which may have from 1 to 3 substituents selected from a halogen atom, a carboxy group, a lower alkoxycarbonyl group, a nitro group, a hydroxy group, a lower alkoxy group and a halogenated lower alkyl group on the phenyl ring thereof include straight chain or branched alkylidene groups of from 1 to 6 carbon atoms containing a phenyl group having, on the phenyl ring thereof, from 1 to 3 substituents selected from a straight chain or branched alkoxy group having from 1 to 6 carbon atoms, a straight chain or branched halogenated alkyl group having from 1 to 6 carbon atoms, a halogen atom, a carboxy group, an alkoxycarbonyl group having from 1 to 6 carbon atoms in the alkoxy moiety, a nitro group, and a hydroxy group, such as 2-chlorobenzylidene, 4-fluorobenzylidene, 2-(3-chlorophenyl)ethylidene, 1-(4-chlorophenyl)ethylidene, 3-(2-fluorophenyl)propylidene, 4-(3-fluorophenyl)butylidene, 1,1-dimethyl-2-(4-fluorophenyl)ethylidene, 5-(2-bromophenyl)pentylidene, 6-(3-bromophenyl)hexylidene, 2-methyl-3-(4-bromophenyl)propylidene, 3-iodobenzylidene, 2-(4-iodophenyl)ethylidene, 1-(3,5-dichlorophenyl)ethylidene, 2-(3,4-dichlorophenyl)ethylidene, 3-(2,6-dichlorophenyl)propylidene, 4-(3,4-dichlorophenyl)butylidene, 1,1-dimethyl-2-(3,4-difluorophenyl)ethylidene, 5-(3,5-dibromophenyl)pentylidene, 6-(3,4,5-trichlorophenyl)hexylidene, 4-fluoromethylbenzylidene, 4-chloromethylbenzylidene, 4-bromomethylbenzylidene, 4-iodomethylbenzylidene, 4-difluoromethylbenzylidene, 4-trifluoromethylbenzylidene, 4-trichloromethylbenzylidene, 2-(2-fluoromethylphenyl)ethylidene, 1-(3-chloromethylphenyl)ethylidene, 3-(3-bromomethylphenyl)propylidene, 4-[4-(2-fluoroethyl)phenyl]butylidene, 5-[4-(2-chloroethyl)phenyl]propylidene, 6-[3-(3-chloropropyl)phenyl]hexylidene, 2-methyl-3-[3-(4-chlorohexyl)phenyl]propylidene, 2-(3,4-difluoromethylphenyl)ethylidene, 2-(2,5-dibromomethylphenyl)ethylidene, 2-(3,4,5-trichloromethylphenyl)ethylidene, 4-methoxybenzylidene, 3,4-dimethoxybenzylidene, 3,4,5-trimethoxybenzylidene, 1-(3-methoxyphenyl)ethylidene, 2-(2-methoxyphenyl)ethylidene, 3-(2-ethoxyphenyl)propylidene, 4-(4-ethoxyphenyl)butylidene, 5-(3-ethoxyphenyl)benzylidene, 6-(4-isopropoxyphenyl)hexylidene, 4-butoxybenzylidene, 1,1-dimethyl-2-(4-hexyloxyphenyl)ethylidene, 2-methyl-3-(3,4-dimethoxyphenyl)propylidene, 2-(3,4-dimethoxyphenyl)ethylidene, 2-(3,4-diethoxyphenyl)ethylidene, 2-(3,4,5-trimethoxyphenyl)ethylidene, 1-(2,5-dimethoxyphenyl)ethylidene, 2-carboxybenzylidene, 3-carboxybenzylidene, 4-carboxybenzylidene, 1-(2-carboxyphenyl)ethylidene, 2-(4-carboxyphenyl)ethylidene, 3-(2,4-dicarboxyphenyl)propylidene, 4-(3-carboxyphenyl)butylidene, 5-(2-carboxyphenyl)pentylidene, 6-(3-carboxyphenyl)hexylidene, 2-nitrobenzylidene, 3-nitrobenzylidene, 4-nitrobenzylidene, 3,4,5-trinitrobenzylidene, 1-(2-nitrophenyl)ethylidene, 2-(4-nitrophenyl)ethylidene, 3-(2,4-dinitrophenyl)propylidene, 4-(3-nitrophenyl)butylidene, 5-(3-nitrophenyl)pentylidene, 6-(3-nitrophenyl)hexylidene, 2-methoxy-3-chlorobenzylidene, 2-hydroxybenzylidene, 2-(3,4-dihydroxyphenyl)ethylidene, 1-(3,4-dihydroxyphenyl)ethylidene, 2-(3-hydroxyphenyl)ethylidene, 3-(4-hydroxyphenyl)propylidene, 6-(3,4-hydroxyphenyl)hexylidene, 2,4-dihydroxybenzylidene, 3,4,5-trihydroxybenzylidene, 4-methoxycarbonylbenzylidene, 3,4-dimethoxycarbonylbenzylidene, 3-(2-ethoxycarbonylphenyl)propylidene, 6-(4-isopropoxycarbonylphenyl)hexylidene, 4-butoxycarbonylbenzylidene, 4-hexyloxycarbonylbenzylidene, etc.

Examples of the phenyl lower alkenylidene group which may have nitro group(s) on the phenyl ring thereof include phenylalkenylidene groups in which the alkenylidene moiety is a straight chain or branched alkenylidene group having from 2 to 6 carbon atoms and which may have from 1 to 3 nitro groups on the phenyl ring thereof, such as phenylvinylidene, 4-nitrophenylvinylidene, 3-phenylallylidene, 3-(4-nitro)-phenylallylidene, 4-phenyl-2-butenylidene, 4-phenyl-3-butenylidene, 1-methyl-3-phenylallylidene, 2-methyl-3-phenylallylidene, 5-phenyl-2-pentenylidene, 6-phenyl-2-hexenylidene, etc.

Examples of lower alkenylidene group include straight chain or branched alkenylidene groups having from 2 to 6 carbon atoms, such as vinylidene, allylidene, 2-butenylidene, 3-butenylidene, 2-pentenylidene, 2-hexenylidene, etc.

Examples of lower cycloalkenylidene group include cycloalkenylidene groups having from 3 to 8 carbon atoms, such as 2-cyclopropenylidene, 2-cyclobutenylidene, 2-cyclopentenylidene, 2-cyclohexenylidene, 2-cycloheptenylidene, 2-cyclooctenylidene, etc.

Examples of the phenoxy lower alkylidene group which may have a carboxy group on the phenyl ring thereof include phenoxyalkylidene groups which may have a carboxy group on the phenyl ring thereof, in which the alkylidene moiety is a straight chain or branched alkylidene group having from 1 to 6 carbon atoms, such as phenoxymethylene, 2-phenoxyethylidene, 1-phenoxyethylidene, 3-phenoxypropylidene, 4-phenoxybutylidene, 1,1-dimethyl-2-phenoxyethylidene, 5-phenoxypentylidene, 6-phenoxyhexylidene, 2-methyl-3-phenoxypropylidene, 2-carboxylphenoxymethylene, 1-(3-carboxyphenoxy)ethylidene, 2-(4-carboxyphenoxy)ethylidene, 3-(2-carboxylphenoxy)propylidene, 4-(3-carboxyphenoxy)butylidene, 1,1-dimethyl-2-(4-carboxylphenoxy)ethylidene, 5-(2-carboxyphenoxy)pentylidene, 6-(3-carboxylphenoxy)hexylidene, 2-methyl-3-(4-carboxylphenoxy)propylidene, etc.

Examples of the phenyl lower alkylidene group which may have a substituent selected from a halogen atom and a halogenated lower alkyl group on the phenyl ring thereof include phenylalkylidene groups containing a straight chain or branched alkylidene moiety having from 1 to 6 carbon atoms, which may have from 1 to 3 substituents selected from a halogen atom and a straight chain or branched halogenated alkyl group having from 1 to 6 carbon atoms on the phenyl ring thereof, such as benzylidene, 2-phenylethylidene, 1-phenylethylidene, 3-phenylpropylidene, 4-phenylbutylidene, 1,1-dimethyl-2-phenylethylidene, 5-phenylpentylidene, 6-phenylhexylidene, 2-methyl-3-phenylpropylidene, 4-fluorobenzylidene, 4-chlorobenzylidene, 4-bromobenzylidene, 4-iodobenzylidene, 2-(2-fluorophenyl)ethylidene, 1-(3-chlorophenyl)ethylidene, 3-(3-bromophenyl)propylidene, 4-fluoromethylbenzylidene, 4-chloromethylbenzylidene, 4-bromomethylbenzylidene, 4-iodomethylbenzylidene, 4-difluoromethylbenzylidene, 4-trifluoromethylbenzylidene, 4-trichloromethylbenzylidene, 2-(2-fluoromethylphenyl)ethylidene, 1-(3-chloromethylphenyl)ethylidene, 3-(3-bromomethylphenyl)propylidene, 4-[4-(2-fluoroethyl)phenyl]butylidene, 5-[4-(2-chloroethyl)phenyl]propylidene, 6-[3-(3-chloropropyl)phenyl]hexylidene, 2-methyl-3-[3-(4-chlorohexyl)phenyl]propylidene, 2-(3,4-difluoromethylphenyl)ethylidene, 2-(2,5-dibromomethylphenyl)ethylidene, 2-(3,4,5-trichloromethylphenyl)ethylidene, etc.

When $R^1$ is a hydrogen atom in the compound of formula (1) of the present invention, the compound may have the following isomer structures (1A) to (1C).

The present invention includes within its scope all of these isomers as well as other steroisomers, optical isomers, and geometrical isomers.

The compounds of formula (1') used in the present invention partially include known compounds, but most of the compounds are novel compounds.

The compounds of formula (1) used in the present invention can be produced by various methods such as, for example, by the methods shown in the following reaction steps I to IX.

Reaction Step I

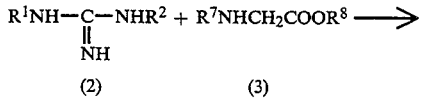

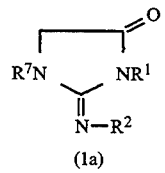

In the above formulae, $R^1$, $R^2$ and $R^7$ have the same meaning as described above, and $R^8$ represents a usual ester residue.

Examples of the ester residue shown by $R^8$ include a lower alkyl group having from 1 to 6 carbon atoms and a phenyl lower alkyl group.

The above-described reaction is carried out in an appropriate solvent at a temperature of from about room temperature to 200° C., and preferably from about 60° C. to 100° C.

Solvents suitable for the above reaction are lower alcohols such as methanol, ethanol or isopropanol; ethers such as dioxane, tetrahydrofuran (THF), ethylene glycol dimethyl ether or diethyl ether; aromatic hydrocarbons such as benzene, toluene or xylene; tertiary amines such as triethylamine or tripropylamine; and polar solvents such as dimethylformamide (DMF) or dimethyl sulfoxide (DMSO).

The amount of the compound shown by formula (3) described above is suitably at least equimolar amount to the compound shown by formula (2), and is preferably from about 1 to 3 molar times the amount of the latter compound.

In general, the reaction is completed within from about 1 to about 24 hours.

Reaction Step II

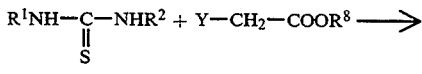

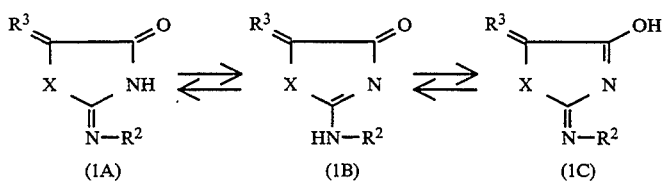

-continued

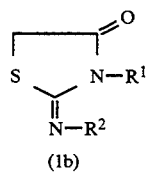

In the above formulae, $R^1$, $R^2$ and $R^8$ have the same meaning as described above, and Y represents a halogen atom.

The above reaction is carried out using a usual solvent in the presence of a deoxidizing agent.

Suitable deoxidizing agents include basic compounds such as potassium carbonate, sodium carbonate, sodium hydroxide, sodium hydrogencarbonate, triethylamine, tripropylamine, pyridine, quinoline, 4-dimethylaminopyridine and sodium acetate.

As the solvent, conventional solvents can be widely used and examples thereof are lower alcohols such as methanol, ethanol or isopropanol; ethers such as dioxane, tetrahydrofuran (THF), ethylene glycol dimethyl ether or diethyl ether; aromatic hydrocarbons such as benzene, toluene or xylene; tertiary amines such as triethylamine or tripropylamine; and polar solvents such as dimethylformamide (DMF) or dimethyl sulfoxide (DMSO). The reaction temperature is suitably from about room temperature to 150° C., and preferably from about 50° C. to 100° C.

The amount of the compound shown by formula (5) described above is suitably at least an equimolar amount to the compound shown by formula (4), and is preferably from about 1 to 3 molar times the amount of the latter compound.

The amount of the deoxidizing agent is from about 1 to 10 molar times, and preferably from about 1 to 3 molar times the amount of the compound shown by formula (4).

The reaction time is generally from about 1 to 24 hours.

Reaction Step III

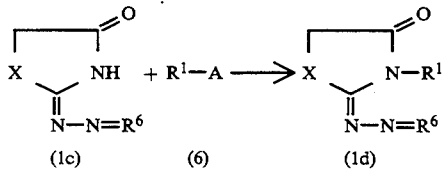

In the above formulae, $R^1$, $R^6$ and X have the same meaning as described above, and A represents a halogen atom.

When $R^1$ is a lower alkyl group, a carboxy lower alkyl group, a lower alkoxycarbonyl lower alkyl group, or a lower cycloalkyl group, the reaction is carried out by a general substitution reaction in the presence of an alkali as a catalyst.

Suitable alkali used in the above reaction include, for example, potassium carbonate, sodium carbonate, sodium hydroxide, sodium hydrogencarbonate, sodium amide, sodium hydride, triethylamine, and tripropylamine.

As the solvent, conventional solvents can be widely used and examples thereof are lower alcohols such as methanol, ethanol or isopropanol; ethers such as dioxane, tetrahydrofuran (THF), ethylene glycol dimethyl ether or diethyl ether; aromatic hydrocarbons such as benzene, toluene or xylene; tertiary amines such as triethylamine or tripropylamine; and polar solvents such as dimethylformamide (DMF) or dimethyl sulfoxide (DMSO).

The reaction temperature is suitably from about 0° to 100° C., and the reaction time is generally from about 1 to about 20 hours.

The ratio of the compound of formula (1c) to the compound of formula (6) is from about 1 to 3 molar times.

The amount of the alkali can be from about 1 to 3 mols per mol of the compound of formula (1c).

In formula (1c), when X is $—N(R^7)$ and $R^7$ is a hydrogen atom, if the reaction is carried out by using an increased molar ratio of the compound of formula (6), e.g., from 2 to 5 molar times the amount of the compound of formula (1c), the above groups shown by $R^1$ and $R^7(=R^1)$ are simultaneously introduced into both the 1-position and the 3-position under the above-described conditions of the substitution reaction.

When $R^1$ is a phenoxy lower alkanoyl group which may have a lower alkoxycarbonyl group on the phenyl ring, the reaction is carried out according to a conventional amido bond-forming reaction, for example, an acid halide method. The acid halide method is carried out in an appropriate solvent in the presence of an deoxidizing agent. The deoxidizing agent may be various deoxidizing agents which can be used for a conventional amido bond-forming reaction, such as, for example, sodium hydrogencarbonate, sodium carbonate, potassium carbonate, pyridine, or triethylamine. As the solvent, conventional solvents such as, for example, water, benzene, chloroform, methylene chloride, carbon tetrachloride, dioxane or tetrahydrofuran can be used.

The ratio of the compound shown by formula (6) is usually at least about an equimolar to the compound of formula (1c), and is preferably from about 1 to 3 molar times the amount of the latter compound. Also, the amount of the deoxidizing agent is from about 1 to 3 mols per mol of the compound of formula (1c). The reaction temperature is usually from about −30° C. to about 100° C., and preferably from about room temperature to 80° C., and the reaction can be completed within from about 20 minutes to about 20 hours.

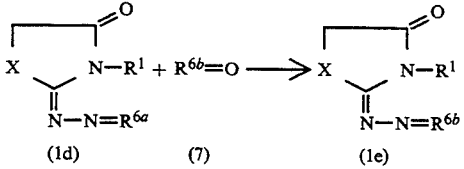

In the above formula IV, $R^1$ and X have the same meaning as described above, $R^{6a}$ represents a lower alkylidene group, and $R^{6b}$ represents a phenyl lower alkylidene group which may have from 1 to 3 substituents selected from a halogen atom, a carboxy group, a nitro group, a hydroxy group, a lower alkoxy group, and a halogenated lower alkyl group on the phenyl ring thereof, a phenyl lower alkenylidene group, or a phenoxy lower alkylidene group which may have a carboxyl group on the phenyl ring thereof.

The above reaction can be carried out in a solvent in the presence of a basic compound or an acidic compound.

As the solvent, acetic acid, benzene, toluene, xylene, methanol, ethanol, propanol, pyridine, picoline, DMF, DMSO, etc., can be used.

The basic compounds which can be used in the above reaction include sodium acetate, potassium carbonate, sodium hydrogencarbonate, sodium alkoxides, etc., and the acidic compounds which can be used include ammonium chloride, ammonium sulfate, concentrated sulfuric acid, etc.

The compound of formula (7) is usually used in an amount of at least about an equimolar amount, and preferably from about 1 to 2 mols per mol of the compound of formula (1d). Also, the basic compound or the acidic compound is used in an amount of from about 1 to 2 mols per mol of the compound of formula (1d).

The reaction temperature is from about room temperature to 150° C., and preferably from about 50° C. to 100° C., and the reaction can be completed within from about 1 to 60 hours.

Reaction Step V

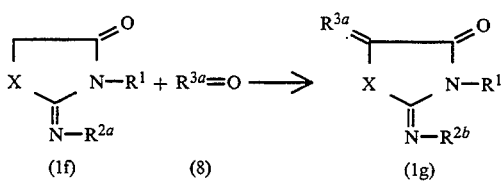

In the above formulae, $R^1$ and X have the same meaning as described above; $R^{2a}$ represents —N=$R^{6a}$, —N=$R^{6b}$, or —NHR$^{4a}$ (wherein $R^{6b}$ is the same as described above, $R^{6a}$ represents a lower alkylidene group, and $R^{4a}$ represents a phenylsulfonyl group which may have from 1 to 3 substituents selected from a halogen atom, a nitro group, a lower alkoxy group, and a lower alkyl group on the phenyl ring thereof); $R^{3a}$ represents a phenyl lower alkylidene group which may have a halogenated lower alkyl group on the phenyl ring thereof or a phenyl lower alkenylidene group; and $R^{2b}$ represents —N=$R^{3a}$, —N=$R^{6b}$, or —NHR$^{4a}$ wherein $R^{3a}$, $R^{6b}$, and $R^{4a}$ are the same as described above.

When $R^{2a}$ in formula (1f) described above is —N=$R^{6a}$, the above reaction is usually carried out by using the compound of formula (8) in an amount of at least about 2 mols, and preferably from about 2 to 3 mols per mol of the compound of formula (1f) in the same manner as in Reaction Step IV, whereby the compound of formula (1g) wherein $R^{2b}$ is —N=$R^{3a}$ can be obtained.

When $R^{2a}$ in formula (1f) is —N=$R^{6b}$ or —NHR$^{4a}$, the reaction is usually carried out by using the compound of formula (8) in an amount of at least about an equimolar amount to the compound of formula (1f), and preferably from about 1 to 2 molar times the amount of the compound of formula (1f) in the same manner as in Reaction Step 4, whereby the compound of formula (1g) wherein $R^{2b}$ is —N=$R^{6b}$ or —NHR$^{4a}$ can be obtained.

Reaction Step VI

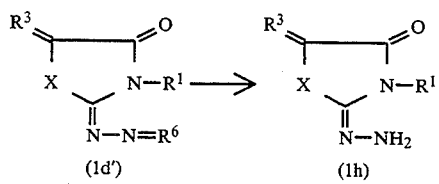

In the above formulae, $R^1$, $R^3$, $R^6$, and X have the same meaning as described above.

The above reaction is carried out in the presence of an organic or inorganic acidic compound. The organic or inorganic acidic compounds which can be used include hydrochloric acid, sulfuric acid, trifluoroacetic acid, acetic acid, formic acid, etc. Of these acidic compounds, a diluted strong acid such as hydrochloric acid or sulfuric acid is particularly preferred.

The solvents which can be used include conventional solvents which are stable to acid, for example, methanol, ethanol, dioxane, tetrahydrofuran or water.

The amount of the acidic compound is from about 1 to 20 molar times that of the compound of formula (1d').

The reaction can be usually carried out at a temperature of from about 30° C. to about 120° C. for about 5 to about 60 minutes.

Reaction Step VII

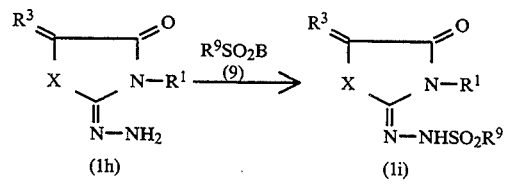

In the above formulae, $R^1$, $R^3$, and X have the same meaning as described above; $R^9$ represents a phenyl group which may have from 1 to 3 substituents selected from a halogen atom, a nitro group, a lower alkoxy group and a lower alkyl group on the phenyl ring thereof; and B represents a halogen atom.

Of the compounds of formula (1) of the present invention, compounds wherein $R^4$ is a phenylsulfonyl group which may have from 1 to 3 substituents selected from a halogen atom, a nitro group, a lower alkoxy group, and a lower alkyl group on the phenyl ring thereof can be synthesized by a usual sulfonation reaction according to Reaction Step VII.

The above reaction is carried out by using a solvent such as diethyl ether, dioxane, tetrahydrofuran or water or a mixture thereof in the presence of an alkali such as potassium carbonate.

The compound of formula (9) is usually used in an amount of from about 1 to 3 mols per mol of the compound (1h). The reaction is usually carried out at a temperature of from about 0° C. to about 60° C. for from about 1 to about 24 hours.

Reaction Step VIII

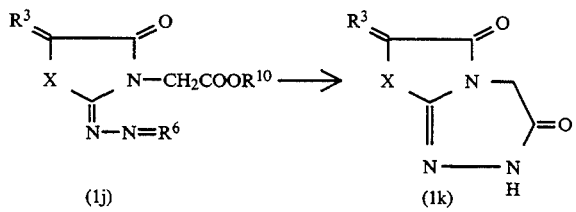

In the above formulae, $R^3$, $R^6$, and X have the same meaning as described above, and $R^{10}$ represents a lower alkyl group.

Reaction Step IX

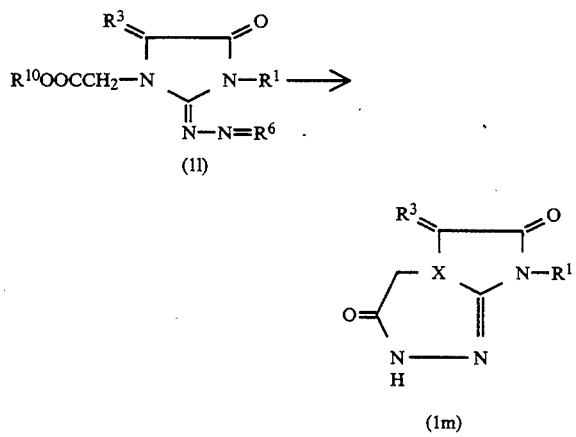

In the above formulae, $R^1$, $R^3$, $R^6$, and X have the same meaning as described above, and $R^{10}$ represents a lower alkyl group.

Reaction Step VIII and Reaction Step IX are reactions for forming an oxoethylene group by bonding of a lower alkoxycarbonylmethyl group and $=N-R^2$ at the 2-position of formula (1) when $R^1$ and/or $R^7$ in the compound of formula (1) is the lower alkoxycarbonylmethyl group.

The above cyclization reactions can be carried out in the same manner as in Reaction Step VI. The reaction is usually carried out at a temperature of from about room temperature to about 150° C., and preferably from about 30° C. to about 120° C. for from about 5 minutes to about 60 minutes.

Also, the reaction can be carried out by sublimating the compound of formula (1j) in vacuum.

The compound of formula (1) wherein $R^1$ or $R^7$ is a lower alkoxycarbonyl lower alkyl group can be converted into a compound having the corresponding carboxy lower alkyl group by a usual hydrolysis of esters. For the above reaction, conventional solvents can be widely used, and examples of the solvent are methanol, ethanol, dioxane, tetrahydrofuran, water, etc.

The reaction is usually carried out at a temperature of from about room temperature to about 120° C., and preferably from about room temperature to about 60° C. for a period of from about 1 hour to about 24 hours. In the reaction, an alkali which is generally used for the hydrolysis of esters can be used, and the preferred examples thereof are sodium hydroxide, potassium hydroxide, etc.

Some of the compounds of formula (4) which are used as starting materials in Reaction Step II described above are unknown compounds, and the production method of these starting material compounds is shown below.

Reaction Step X

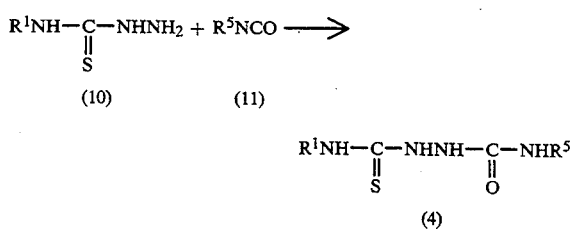

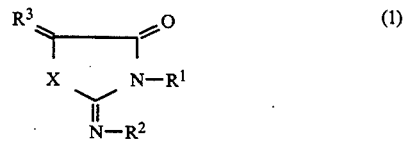

In the above formulae, $R^1$ and $R^5$ have the same meaning as described above.

The above reaction is carried out in an inert solvent such as diethyl ether, tetrahydrofuran, dioxane, water or a mixture thereof. The compound of formula (11) is usually used in an amount of from about 1 to 3 mols per mol of the compound of formula (10). The reaction is usually carried out at a temperature of from about 0° C. to about 50° C. for a period of from about 1 hour to about 20 hours.

Of the compounds of the present invention, the compounds represented by the following formula (1) are novel compounds:

$$\text{(1)}$$

wherein $R^1$ represents a hydrogen atom, a lower alkyl group, a carboxy lower alkyl group, a lower alkoxycarbonyl lower alkyl group, a phenoxy lower alkanoyl group which may have a lower alkoxycarbonyl group on the phenyl ring thereof, or a lower cycloalkyl group; $R^2$ represents $-NHR^4$ (wherein $R^4$ represents a hydrogen atom, a phenylsulfonyl group which may have from 1 to 3 substituents selected from a halogen atom, a nitro group, a lower alkoxy group and a lower alkyl group on the phenyl ring thereof, a phenyl lower alkanoyl group, or $-CO-NHR^5$ (wherein $R^5$ represents a lower alkyl group, a phenyl group which may have a halogen atom on the phenyl ring thereof, a phenyl lower alkyl group, or a naphthyl group)), or $-N=R^6$ (wherein $R^6$ represents a lower alkylidene group, a lower alkylidene group having 1 or 2 lower cycloalkyl groups, a phenyl lower alkylidene group which may have from 1 to 3 substituents selected from a halogen atom, a carboxy group, a lower alkoxycarbonyl group, a nitro group, a hydroxy group, a lower alkoxy group and a halogenated lower alkyl group on the phenyl ring thereof, a phenyl lower alkenylidene group which may have a nitro group on the phenyl ring thereof, a lower alkenylidene group, a lower cycloalkylidene group, or a phenoxy lower alkylidene group which may have a carboxy group on the phenyl ring thereof); $R^3$ represents two hydrogen atoms, a phenyl lower alkylidene group which may have a halogen atom or a halogenated lower alkyl group on the phenyl ring thereof, or a phenyl lower alkenylidene group; and X represents $-S-$ or $-N(R^7)-$ (wherein $R^7$ represents a hydrogen atom, a lower alkyl group, a carboxy lower alkyl group, or a lower alkoxycarbonyl lower alkyl group; and R¹ and R⁴, or R⁴ and R⁷ may combine with each other to form an oxoethylene group, with the provisos that, when R¹ is a hydrogen atom, R³ is two hydrogen atoms, and X is —S—, then R² should not be —NHR⁴ (wherein R⁴ is a hydrogen atom or a phenylsulfonyl group which may have a lower alkoxy group on the phenyl ring thereof) or —N=R⁶ (wherein R⁶ represents a lower alkylidene group, a phenyl lower alkylidene group which may have a halogen atom, a nitro group, a hydroxy group, or a lower alkoxy group on the phenyl ring thereof, or a phenyl lower alkenylidene group which may have a nitro group on the phenyl ring thereof); that, when R¹ is a hydrogen atom, R² is —N=R⁶, and X is —S— or —NH—, then R³ and R⁶ should not simultaneously be a phenyl lower alkylidene group, and further that, when R² is —NHR⁴, R³ is two hydrogen atoms, and X is —S—, R¹ and R⁴ should not combine with each other to form an oxoethylene group.

The compounds of the present invention include pharmaceutically acceptable addition salts thereof formed with acids or basic compounds.

These salts can be easily formed by reacting an acid or a base shown below with the compound of the present invention. The acids used for forming the salt include, for example, inorganic acids such as hydrochloric acid, sulfuric acid, phosphoric acid, hydrobromic acid, etc., and, as the case may be, organic acids such as oxalic acid, maleic acid, fumaric acid, malic acid, tartaric acid, citric acid, benzoic acid, etc. Also, the basic compounds used for forming the salts include, for example, sodium hydroxide, potassium hydroxide, calcium hydroxide, sodium carbonate, potassium hydrogencarbonate, etc.

The compound of formula (1) produced by each method described above and the salt thereof can be easily isolated from the reaction system and purified by a conventional separation means such as a distillation method, a recrystallization method, a column chromatography, a preparative thin-layer chromatography, a solvent extraction method, etc.

The Maillard reaction inhibitor of the present invention is usually used in the form of a general pharmaceutical preparation.

The preparation is prepared by using a diluent or an excipient such as a filler, an extender, a binder, a humidifying agent, a disintegrating agent, a surface active agent, a lubricant, etc.

As the pharmaceutical preparation, various forms can be selected according to the purposes of treatment. Typical examples thereof are tablets, pills, powders, liquids, suspensions, emulsions, granules, capsules, supositories, injections (liquids, suspensions, etc.), ointments, etc.

For forming tablets, excipients such as lactose, sucrose, sodium chloride, glucose, urea, starch, calcium carbonate, kaolin, crystalline cellulose, silicic acid, etc.; binders such as water, ethanol, propanol, simple syrup, a glucose solution, a starch solution, a gelatin solution, carboxymethyl cellulose, shellac, methyl cellulose, potassium phosphate, polyvinyl pyrrolidone, etc.; disintegrating agents such as dry starch, sodium alginate, an agar powder, a laminaran powder, sodium hydrogencarbonate, calcium carbonate, polyoxyethylene sorbitan fatty acid esters, sodium laurylsulfate, stearic acid monoglyceride, starch, lactose, etc.; disintegration inhibitors such as sucrose, stearin, cacao butter, a hydrogenated oil, etc.; absorption accelerators such as quaternary ammonium bases, sodium laurylsulfate, etc.; moisture keeping agents such as glycerol, starch, etc.; absorbents such as starch, lactose, kaolin, benzonite, colloidal silicic acid, etc.; lubricants such as purified talc, stearates, a boric acid powder, polyethylene glycol, etc., can be used as carriers. Furthermore, if necessary, the tablets may applied with ordinary coating to form, for example, sugar-coated tablets, gelatin-coated tablets, enteric coated tablets, film-coated tablets, double coated tablets, and multilayer tablets.

For forming pills, excipients such as glucose, lactose, starch, cacao butter, hardened vegetable oils, kaolin, talc, etc.; binders such as a gum arabic powder, a tragacanth rubber powder, gelatin, ethanol, etc.; disintegrating agents such as laminaran, agar, etc.; can be used as carriers.

For forming suppositories, polyethylene glycol, cacao butter, higher alcohols, higher alcohol esters, gelatin, semi-synthetic glyceride, etc., can be used as carriers.

The preparation of capsules is carried out by a conventional method by mixing the compound of this invention with various carriers described above and filling the mixture in hard gelatin capsules, hard capsules, etc.

In the case of preparing injections, liquids, emulsions, or suspensions are sterilized and preferably made isotonic to blood. For preparing the injections, water, an aqueous lactic acid solution, ethanol, propylene glycol, ethoxylated isostearyl alcohol, polyoxyethylene sorbitan fatty acid esters, etc., can be used as a diluent. In this case, for preparing an isotonic solution, a sufficient amount of sodium chloride, glucose, or glycerol may be incorporated in the pharmaceutical preparation or an ordinary dissolution aid, a buffer, a pain alleviating agent, etc., may be added thereto. Furthermore, if necessary, a coloring agent, a preservative, a perfume, a flavoring agent, sweetening agent, etc., and other pharmaceutical agents may be incorporated in the pharmaceutical preparation.

For forming pastes, creams, and gels, white vaseline, paraffin, glycerol, a cellulose derivative, polyethylene glycol, silicone, bentonite, etc., can be used as a diluent.

The amount of the compound of this invention being contained in the pharmaceutical preparation of this invention can be properly selected in a wide range without being restrained but is usually from 1 to 70% by weight in the pharmaceutical preparation.

There is no particular restriction on the administration method of the pharmaceutical preparation of the present invention, and the various methods can be selected according to the age, sex, and other conditions of patients, the state of the disease, and the form of the preparation, the pharmaceutical preparation is usually administrated systemically or topically by oral or parenteral administration.

For example, the compound of the preparation is orally administrated in the forms of tablets, pills, liquids, suspensions, emulsions, granules, or capsules or is administrated in the form of injections or as a mixture with other ordinary auxiliary liquid by intravenous injection, intramuscular injection, intracutaneous injection, subcutaneous injection, or intraperitoneal injection.

In other methods, the preparation can be administrated in the rectum as a suppository or can be applied as an ointment.

The dosage of the pharmaceutical preparation of the present invention is properly selected according to the age, weight, conditions of diseases, treatment effect, administration method, treating time, etc. of patients, but is usually administrated at a dose in the range of from about 0.1 to 100 mg per kg of body weight per day. The preparation may be administrated once to several times per day. As the matter of course, the dosage level changes by various conditions. Thus, as the case may be, the dosage may be less than the above-described range or over the range.

Then, the productions of the compounds for use in this invention are shown below as examples and the phamacological test results of these compounds and examples of preparations are shown below.

EXAMPLE 1

(1) To a methanol solution of sodium methoxide prepared by dissolving 1.61 g of sodium metal in 100 ml of methanol was added 4.00 g of isopropylideneaminoguanidine, and, after stirring the mixture for one hour at room temperature, 5.88 g of glycine ethyl ester hydrochloride was added thereto, followed by refluxing under heating for 16 hours. After cooling the reaction mixture, water and chloroform were added thereto to distribute the mixture between water and chloroform and, then, the aqueous layer was extracted three times with chloroform.

The organic layer was combined with the extract. After drying the mixture over anhydrous magnesium sulfate, the mixture was concentrated under reduced pressure, the residue was charged on silica gel column chromatography and eluted with a mixed solvent of chloroform and methanol of 100:1 by volume to provide 0.81 g of 2-isopropylidenehydrazonoimidazolidin-4-one as white crystals.

NMR (CD$_3$OD) δ ppm: 3.93 (s, 2H) 1.99 (d, J=5.71 Hz, 6H) m.p. 182° to 187° C.

By following the similar procedure to above (1), the following compounds were obtained.

(2) 2-Benzylidenehydrazonoimidazolidin-4-one
m.p. 246° to 248° C.

(3) 2-α-Methylcinnamyridenehydrazonoimidazolidin-4-one
m.p. 243° to 245° C.

(4) 2-Cyclopentylidenehydrazonoimidazolidin-4-one
NMR (DMSO-d$_6$) δ: 3.75 (s, 2H) 2.29–2.49 (m, 4H) 1.65–1.88 (m, 4H)

(5) 2-(1-Cyclopropylethylidenehydrazono)imidazolidin-4-one
m.p. 169° to 172° C.
NMR (DMSO-d$_6$) δ: 3.81 (s, 2H) 1.74 (s, 3H) 1.50–1.63 (m, 1H) 0.64–0.85 (m, 4H)

(6) 2-Cyclohexylmethylenehydrozonoimidazolidin-4-one
NMR (DMSO-d$_6$) δ: 7.36 (d, J=5.61 Hz, 1H) 3.26 (s, 2H) 2.17–2.29 (m, 1H) 1.64–1.75 (m, 4H) 1.15–1.30 (m, 5H)

(7) 2-Cyclohexylidenehydrazonoimidazolidin-4-one
NMR (DMSO-d$_6$) δ: 3.97 (s, 2H) 2.50–2.53 (m, 2H) 2.28–2.53 (m, 2H) 1.66–1.69 (m, 6H)

(8) 2-n-Butylidenehydrazonoimidazolidin-4-one
m.p. 158° to 162° C.
NMR (DMSO-d$_6$) δ: 7.47 (t, J=5.61 Hz, 1H) 3.76 (s, 2H) 2.16–2.29 (m, 2H) 1.41–1.57 (m, 2H) 0.90 (t, J=7.26 Hz, 3H)

(9) 2-Dicyclopropylmethylenehydrazonoimidazolidin-4-one
NMR (DMSO-d$_6$) δ: 3.79 (s, 2H) 0.47–1.06 (m, 10H)

(10) 2-(1-Trifluoromethylethylidenehydrazono)imidazolin-4-one
NMR (DMSO-d$_6$) δ: 11.28 (s, 1H) 7.79 (s, 1H) 3.98 (s, 2H) 2.06 (s, 3H)

(11) 2-Hexafluoroisopropylidenehydrazonoimidazolin-4-one
NMR (DMSO-d$_6$) δ: 3.99 (s, 2H)

EXAMPLE 2

(1) To a methanol solution of sodium methoxide prepared by dissolving 2.30 g of sodium metal in 150 ml of methanol was added 5.70 g of benzylideneaminoguanidine and, after stirring the mixture for one hour at room temperature, 11.35 g of iminodiacetic acid diethyl ester was added thereto, followed by refluxing under heating for 17 hours.

After cooling the reaction mixture, water and chloroform were added to the reaction mixture to distribute the mixture between water and chloroform. After recovering the organic layer, the aqueous layer was extracted three times with chloroform. The organic layer was combined with the extract. After drying the mixture over anhydrous magnesium sulfate, the mixture was concentrated under reduced pressure, the residue formed was charged on silica gel column chromatography and eluted with a mixed solvent of chloroform and methanol of 100:1 by volume to obtain 2.61 g of 2-benzylidenehydrazono-1-methoxycarbonylmethylimidazolidin-4-one.

m.p. 149° to 153° C.
NMR (CDCl$_3$) δppm: 8.26 (s, 1H) 7.32 to 7.68 (m, 5H) 4.23 (s, 2H) 4.01 (s, 2H) 3.77 (s, 3H)

(2) To 2.61 g of the compound obtained in the above step was added 40 ml of methanol and 14 ml of a 2N sodium hydroxide solution, and the mixture was stirred for 4 hours at room temperature. The reaction mixture obtained was concentrated under reduced pressure. After adding 10 ml of water to the residue, the mixture was neutralized with 1N hydrochloric acid. Insoluble materials were recovered by filtration and washed with water and diethyl ether to obtain 1.82 g of 2-benzylidenehydrazono-1-carboxymethylimidazolidin-4-one.

m.p. 218° to 222° C.
NMR (DMSO-d$_6$) δ ppm: 11.37 (brs, 1H) 8.16 (s, 1H) 7.34 to 7.86 (m, 5H) 4.08 (s, 2H) 4.02 (s, 2H)

By following the similar procedure to above step, the following compounds were obtained.

(3) 2-Isopropylidenehydrazono-1-methoxycarbonylmethylimidazolidin-4-one
NMR (CDCl$_3$) δ ppm: 4.15 (s, 2H) 4.02 (s, 2H) 3.76 (s, 3H) 1.97 (s, 3H) 1.94 (s, 3H)

(4) 1-methoxycarbonylmethyl-2-α-methylcinnamyridenehydrazonoimidazolidin-4-one
NMR (CDCl$_3$) δ ppm: 8.40 (s, 1H) 7.26 (s, 5H) 6.72 (s, 1H) 4.22 (s, 2H) 4.09 (s, 2H) 3.78 (s, 3H)

(5) 2-(4-Carboxybenzylidenehydrazono)-1-carboxymethylimidazolidin-4-one
m.p. 205° to 209° C.
NMR (DMSO-d$_6$) δ ppm: 11.47 (brs, 1H) 8.20 (s, 1H) 7.49 (brs, 4H) 4.08 (s, 2H) 3.84 (s, 2H)

EXAMPLE 3

(1) A mixture of 154 mg of 2-isopropylidenehydrazonoimidazolidin-4-one, 198 mg of sodium acetate, 5 ml of acetic acid, and 317 mg of cinnamic aldehyde was stirred for 19 hours at 60° C. To the reaction mixture were added water and chloroform to distribute the mixture between them, and then the aqueous layer was further extracted three times with chloroform. The organic layer was combined with the extract. After drying the mixture over anhydrous magnesium sulfate, the mixture was concentrated under reduced pressure, the residue formed was charged on silica gel column chromatography and eluted with a mixed solvent of chloroform and ethyl acetate at 1:1 by volume to obtain 62 mg of 2-cinnamylidenehydrazono-5-cinnamylideneimidazolidin-4-one having melting point of from 154° C. to 156° C.

By following the similar procedure to the above step, the following compounds were obtained.

(2) 2-Benzylidenehydrazono-5-benzylidenethiazolidin-4-one

NMR (DMSO-$d_6$) δ ppm: 8.49 (s, 1H) 7.21 to 7.93 (m, 11H)

(3) 2-Cinnamylidenehydrazono-5-cinnamylidenethiazolidin-4-one

NMR (DMSO-$d_6$) δ ppm: 12.35 (brs, 1H) 8.26 (d, J=8, 13 Hz, 1H) 6.79 to 7.68 (m, 15H)

(4) 2-(4-Trifluoromethylbenzylidenehydrazono)-5-(4-trifluoromethylbenzylidene)thiazolidin-4-one NMR (DMSO-$d_6$) δ ppm: 8.61 (s, 1H) 7.67 to 8.07 (m, 9H)

EXAMPLE 4

(1) A mixture of 1.10 g of 2-benzylidenehydrazono-1-methoxycarbonylmethylimidazolidin-4-one, 520 mg of sodium acetate, 10 ml of acetic acid, and 1.34 g of cinnamic aldehyde was stirred for 16 hours at a temperature of from 60° C. to 70° C.

After cooling the reaction mixture, water and ethyl acetate were added thereto to distribute the mixture between water and ethyl acetate, and the aqueous layer was further extracted three times with ethyl acetate. The organic layer was combined with the extract. After drying the mixture over anhydrous magnesium sulfate, the mixture was concentrated under reduced pressure, the residue was charged on silica gel column chromatography and eluted with a mixed solvent of n-hexane and ethyl acetate at 1:1 by volume to obtain 620 mg of 2-cinnamylidenehydrazono-5-cinnamylidene-1-methoxycarbonylmethylimidazolidin-4-one.

NMR (CDCl$_3$) δ ppm: 8.02 to 8.33 (m, 2H) 7.18 to 7.78 (m, 12H) 6.69 (d, J=15, 8 Hz, 1H) 5.95 (d, J=11, 4 Hz, 1H) 4.53 (s, 2H) 3.81 (s, 3H)

(2) To 620 mg of the compound obtained in the above step were added 20 ml of methanol and 2.4 ml of a 2N sodium hydroxide solution, and the mixture was stirred for 24 hours at room temperature. The reaction mixture obtained was neutralized with the addition of 1N hydrochloric acid. Then, the reaction mixture was concentrated under reduced pressure and recrystallized from ethanol to obtain 417 mg of 1-carboxymethyl-2-cinnamylidenehydrazono-5-cinnamylideneimidazolidin-4-one having a melting point of from 246° C. to 248° C.

EXAMPLE 5

(1) After dissolving 2.73 g of thiosemicarbazide in a mixture of 80 ml of tetrahydrofuran and 20 ml of water, 3.57 g of phenyl isocyanate was added to the solution, followed by stirring for 6 hours at room temperature. The reaction mixture obtained was concentrated under reduced pressure, after adding 100 ml of water to the residue formed, precipitates thus formed were ground, filtered, washed with water, and then recrystallized from methanol to obtain 1.80 g of white crystals.

(2) The crystals obtained in the above step were dissolved in 80 ml of ethanol and, after adding 1.26 g of ethyl chloroacetate and 840 mg of sodium sulfate, the resulting mixture was refluxed under heating for 16 hours. The reaction product obtained was cooled, and the precipitated crystals were recovered by filtration to obtain 1.65 g of 2-(4-phenylsemicarbazono)thiazolidin-4-one.

NMR (DMSO-$d_6$) δ ppm: 11.64 (brs, 1H) 9.01 (s, 1H) 8.92 (s, 1H) 6.82 to 7.52 (m, 5H) 3.91 (s, 2H)

By following the similar procedure to the above step, the following compounds were obtained.

(3) 2-(4-Naphthylsemicarbazono)thiazolidin-4-one

NMR (DMSO-$d_6$) δ ppm: 11.56 (brs, 1H) 9.12 (s, 1H) 8.69 (s, 1H) 7.35 to 8.07 (m, 7H) 3.97 (s, 2H)

(4) 2-[4-(4-Chlorophenyl)semicarbazono)thiazolidin-4-one

NMR (DMSO-$d_6$) δ ppm: 11.47 (brs, 1H) 9.02 (s, 2H) 7.50 (d, J=9.01 Hz, 2H) 7.26 (d, J=8.79 Hz, 2H) 3.92 (s, 2H)

(5) 2-(4-Benzylsemicarbazono)thiazolidin-4-one
m.p.: 218° C. to 220° C.

(6) 2-[4-(4-Fluorophenyl)semicarbazono]thiazolidin-4-one
m.p.: 223° C. to 225° C.

(7) 2-(4-Butylsemicarbazono)thiazolidin-4-one

NMR (DMSO-$d_6$) δ ppm: 11.43 (brs, 1H) 8.56 (s, 1H) 6.41 (t, J=5.9 Hz, 1H) 3.88 (s, 2H) 2.87 to 3.19 (m, 2H) 1.25 (brs, 4H) 0.88 (t, J=6.3 Hz, 3H)

EXAMPLE 6

(1) To 226 mg of 2-isopropylidenehydrazono-1-methoxycarbonylmethylimidazolidin-4-one were added 10 ml of methanol and 1 ml of a 2N sodium hydroxide solution, and the mixture was stirred for 16 hours at room temperature. The reaction mixture obtained was neutralized with the addition of 1N hydrochloric acid, concentrated under reduced pressure, and the residue formed was recrystallized from methanol to obtain 75 mg of 1,4,5,7-tetraazabicyclo[4,3,0]nonan-5-ene-3,8-dione.
m.p. higher than 300° C.

NMR (DMSO-$d_6$) δ ppm: 11.00 (brs, 1H) 11.07 (brs, 1H) 3.79 (s, 2H) 3.73 (s, 2H)

EXAMPLE 7

(1) In 20 ml of dimethylformamide (DMF) was suspended 96 mg of 60% sodium hydride under ice-cooling, 5 ml of a DMF solution of 548 mg of 2-benzylidenehydrazono-1-methoxycarbonylmethylimidazolidin-4-one was gradually added to the suspension. After stirring the mixture for one hour at 30° C., 254 mg of ethyl chloroacetate was gradually added dropwise thereto, followed by stirring for one hour at 80° C. After cooling the reaction mixture, water and chloroform was added thereto to distribute the mixture between water and chloroform, and the aqueous layer was further extracted three times with chloroform. The organic layer was combined with the extract, the mixture was dried over anhydrous magnesium sulfate, concentrated under reduced pressure, and the residue formed was recrystallized from a mixture of chloroform and n-hexane to obtain 320 mg of 2-benzylidenehydrazono-3-ethoxycarbonylmethyl-1-methoxycarbonylmethylimidazolidin-4-one.

NMR (CDCl$_3$) δ ppm: 8.13 (s, 1H) 2.75 to 7.60 (m, 5H) 4.71 (s, 2H) 4.41 (s, 2H) 4.14 (s, 2H) 4.17 (q, J=5.9 Hz, 2H) 3.71 (s, 3H) 1.29 (t, J=7.0 Hz, 3H)

(2) To the compound obtained in the above step were added 15 ml of methanol and 3 ml of a 2N sodium hydroxide solution, and the mixture was stirred for 2 hours at room temperature. The reaction mixture obtained was concentrated under reduced pressure, and after adding 3 ml of water to the residue formed, the mixture was neutralized with 1N hydrochloric acid. Insoluble materials were filtered off, and the filtrate was concentrated again under reduced pressure and recrystallized from methanol to obtain 180 mg of 2-benzylidenehydrazono-1,3-dicarboxymethylimidazolidin-4-one.

NMR (DMSO-d$_6$) δ ppm: 8.12 (s, 1H) 7.33 to 7.79 (m, 5H) 4.67 (s, 2H) 4.26 (s, 2H) 4.19 (s, 2H)

EXAMPLE 8

(1) To 230 mg of 2-benzylidenehydrazono-3-ethoxycarbonylmethyl-1-methoxycarbonylmethylimidazolidin-4-one obtained in step (1) of Example 7 was added 10 ml of 0.5N hydrochloric acid, the mixture was subjected to a steam distillation for 40 minutes. The reaction mixture obtained was concentrated under reduced pressure, and the residue formed was charged on silica gel column chromatography and eluted with a mixture of chloroform and ethyl acetate at 1:2 by volume to obtain 60 mg of 7-ethoxycarbonylmethyl-1,4,5,7-tetraazabicyclo[4,3,0]-nonan-5-ene-3,8-dione.

m.p. 188° to 193° C.

NMR (DMSO-d$_6$) δ ppm: 10.24 (s, 1H) 4.20 (s, 2H) 4.04 (q, J=6.91 Hz, 2H) 3.98 (s, 2H) 1.20 (t, J=6.81 Hz, 3H)

(2) To the compound obtained above were added 5 ml of ethanol and 0.3 ml of a 2N sodium hydroxide solution, and the mixture was stirred for 2 hours at room temperature. The reaction mixture obtained was concentrated under reduced pressure, the residue formed was dissolved in water. The resulting solution was neutralized with 1N hydrochloric acid and concentrated again under reduced pressure. The residue formed was recrystallized from methanol to obtain 29 mg of 7-carboxymethyl-1,4,5,7-tetraazabicyclo[4,3,0]nonan-5-ene-3,8-dione.

NMR (DMSO-d$_6$) δ ppm: 8.44 (brs, 1H) 4.33 (s, 2H) 4.09 (s, 2H) 3.93 (s, 2H)

EXAMPLE 9

(1) In 20 ml of DMF was suspended 192 mg of 60% sodium hydride under ice-cooling, about 5 ml of a DMF solution of 716 mg of 2-isopropylidenehydrazonothiazolidin-4-one was gradually added to the suspension, and, after stirring the mixture for 30 minutes, 588 mg of ethyl chloroacetate was gradually added dropwise to the mixture, followed by stirring for 3 hours at room temperature.

To the reaction mixture obtained were added water and chloroform to distribute the mixture between water and chloroform, and the organic layer was washed twice with water and dried over anhydrous magnesium sulfate. The aqueous layer was concentrated under reduced pressure, the residue formed was charged on silica gel column chromatography and eluted with a mixture of chloroform and ethyl acetate at 10:1 by volume to obtain 870 mg of 3-ethoxycarbonylmethyl-2-isopropylidenehydrazonothiazolidin-4-one having a melting point of 60° to 62° C.

NMR (CDCl$_3$) δ ppm: 4.49 (s, 2H) 4.21 (q, J=7.03 Hz, 2H) 3.82 (s, 2H) 2.01 (d, J=6.38 Hz, 6H) 1.26 (t, J=7.25 Hz, 3H)

(2) To 870 mg of the compound obtained above were added 20 ml of methanol and 3 ml of an aqueous sodium hydroxide solution under ice-cooling, and the mixture was stirred for one hour. The reaction mixture obtained was neutralized with the addition of 1N hydrochloric acid, concentrated under reduced pressure, and the residue was recrystallized from ethanol to obtain 280 mg of 3-carboxymethyl-2-isopropylidenehydrazonothiazolidin-4-one.

NMR (DMSO-d$_6$) δ ppm: 3.97 (s, 2H) 3.81 (s, 2H) 1.97 (s, 6H)

By following the similar procedure to the above steps (1) and (2) using appropriate starting materials, the following compounds were obtained.

(3) 5-Benzylidene-2-benzylidenehydrazone-3-carboxymethylthiazolidin-4-one m.p. higher than 300° C.

NMR (DMSO-d$_6$) δ ppm: 8.53 (s, 1H) 7.50 to 7.81 (m, 11H) 4.16 (s, 2H)

(4) 3-(3-Carboxypropyl)-2-cinnamylidenehydrazono-5-cinnamylidenethiazolidin-one

NMR (DMSO-d$_6$) δ ppm: 7.12 (d, J=9.01 Hz, 1H) 6.81 to 7.83 (m, 15H) 3.93 (t, J=6.1 Hz, 2H) 1.71 to 2.38 (m, 4H)

(5) 3-(5-Carboxypentyl)-2-cinnamylidenehydrazono-5-cinnamylidenethiazolidin-4-one NMR (CDCl$_3$) δ ppm: 8.21 (s, 1H) 6.83 to 7.59 (m, 15H) 3.91 (t, J=6.03 Hz, 2H) 1.44 to 2.54 (m, 8H)

EXAMPLE 10

(1) To 2.0 g of 3-ethoxycarbonylmethyl-2-isopropylidenehydrazonothiazilidin-4-one obtained in step (1) of Example 9 was added 30 ml of 0.5N hydrochloric acid, and the mixture was subjected to steam distillation for 15 minutes. The reaction mixture obtained was cooled, the resulting precipitates were distilled off, and the filtrate was concentrated under reduced pressure. To the residue formed were added a saturated sodium hydrogencarbonate solution and chloroform to distribute the residue between them. The organic layer was washed three times with water, dried over anhydrous magnesium sulfate, and concentrated under reduced pressure. The residue formed was charged on silica gel column chromatography and eluted with a mixture of chloroform and ethyl acetate at 4:1 by volume to obtain 870 mg of 3-ethoxycarbonylmethyl-2-hydrazonothiazolidin-4-one.

NMR (DMSO-d$_6$) δ ppm: 5.26 (s, 2H) 4.29 (s, 2H) 4.12 (q, J=7.03 Hz, 2H) 1.19 (t, J=7.04 Hz, 3H)

(2) Also, the saturated sodium hydrogencarbonate solution layer was combined with the aqueous solution layer, the mixture was concentrated under reduced pressure, and the residue formed was suspended in ethanol. Insoluble materials were filtered off, and the filtrate was concentrated under reduced pressure and recrystallized from water to obtain 315 mg of 2H-thiazolo[2,3-c][1,2,4]triazine-3,6(4H, 7H)-dione as a cyclized product.

NMR (DMSO-d$_6$) δ ppm: 10.79 (s, 1H) 4.09 (s, 4H)

(3) After adding 15 ml of dioxane, 3 ml of water, 76 mg of potassium carbonate, and 300 mg of 2,4-dinitrobenzenesulfonyl chloride to 200 mg of the compound obtained in the above step (1) under ice-cooling, the mixture was stirred for one hour at room temperature. The reaction mixture obtained was concentrated under reduced pressure, the residue formed was charged on silica gel column chromatography and eluted with a mixture of chloroform and ethyl acetate at 1:1 by volume ratio to obtain 2-(2,4-dinitrobenzenesulfonohydrazono)-3-ethoxycarbonylmethylthiazolidin-4-one having a melting point of 163° to 165° C.

NMR (CDCl$_3$) $\delta$ ppm: 8.63 (s, 1H) 8.54 (d, J=8.57 Hz, 1H) 8.26 (d, J=8.35 Hz, 1H) 4.29 (s, 2H) 4.14 (q, J=7.01 Hz, 2H) 3.92 (s, 2H) 1.24 (t, J=7.04 Hz, 3H)

(4) To 180 mg of the compound obtained in the above step (3) were 5 ml of ethanol and 0.5 ml of an aqueous sodium hydroxide solution, and the mixture was stirred for 20 hours at room temperature. The reaction mixture was concentrated under reduced pressure. After adding water to the residue formed, the resulting solution was neutralized with the addition of 1N hydrochloric acid. Insoluble materials were recovered by filtration and washed with water and diethyl ether to obtain 130 mg of 3-carboxymethyl-2-(2,4-dinitrobenzenesulfonohydrazono)thiazolidin-4-one.

NMR (DMSO-d$_6$) $\delta$ ppm: 8.86 (s, 1H) 8.63 (d, J=8.57 Hz, 1H) 8.23 (d, J=8.57 Hz, 1H) 4.21 (s, 2H) 4.14 (s, 2H)

By following the similar procedure to the above steps (3) and (4), the following compounds were obtained.

(5) 3-Carboxymethyl-2-(2-nitrobenzenesulfonohydrazono)thiazolidin-4-one

NMR (CD$_3$OD) $\delta$ ppm: 7.59 to 8.04 (m, 4H) 4.21 (s, 2H) 3.95 (s, 2H)

(6) 2-(4-Bromobenzenesulfonohydrazono)-3-carboxymethylthiazolidin-4-one

NMR (CD$_3$OD) $\delta$ ppm: 7.74 (s, 4H) 4.32 (s, 2H) 3.98 (s, 2H)

(7) 3-Ethoxycarbonylmethyl-2-phenylacetylhydrazonothiazolidin-4-one m.p. 200° to 203° C.

NMR (CDCl$_3$) $\delta$ ppm: 7.24 (s, 5H) 4.58 (s, 2H) 4.19 (q, J=7.0 Hz, 2H) 4.01 (s, 2H) 3.72 (s, 2H) 1.23 (t, J=6.9 Hz, 3H)

(8) 3-Ethoxycarbonylmethyl-2-(4-methoxybenzenesulfonohydrazono)thiazolidin-4-one NMR (CDCl$_3$) $\delta$ ppm: 7.80 (d, J=8.79 Hz, 2H) 6.95 (d, J=8.79 Hz, 2H) 4.35 (s, 2H) 4.13 (q, J=7.25 Hz, 2H) 3.86 (s, 5H) 1.22 (t, J=7.0 Hz, 3H)

EXAMPLE 11

(1) To 1.03 g of 3-ethoxycarbonylmethyl-2-isopropylidenehydrazonothiazolidin-4-one obtained in step (1) of Example 9 were added 984 mg of sodium acetate, 10 ml of acetic acid, and 2.54 g of cinnamaldehyde, and the resulting mixture was stirred for 16 hours at a temperature of from 110° C. to 120° C. To the reaction mixture obtained was added 20 ml of water, and the resulting precipitates were recovered by filtration and recrystallized from a mixture of benzene and n-hexane to obtain 810 mg of 3-ethoxycarbonylmethyl-2-cinnamylidenehydrazono-5-cinnamylidenethiazolidin-4-one as light yellow crystals. The melting point thereof was from 210° C. to 212° C.

(2) Then, by following the similar procedure to step (2) of Example 2,3-carboxymethyl-2-cinnamylidenehydrazono-5-cinnamylidenethiazolidin-4-one was obtained.

m.p. higher than 300° C.

NMR (DMSO-d$_6$) $\delta$ ppm: 8.29 (d, J=8.13 Hz, 1H) 6.89 to 7.72 (m, 15H) 4.48 (s, 2H)

By following the similar procedure to the above step, the following compound was obtained.

(3) 3-Carboxymethyl-2-(4-fluorobenzylidenehydrazono)-5-(4-fluorobenzylidene)thiazolidin-4-one NMR (DMSO-d$_6$) $\delta$ ppm: 8.53 (s, 1H) 7.22 to 7.89 (m, 9H) 4.13 (s, 2H)

EXAMPLE 12

(1) To 1.31 g of 2-hydrazonothiazolidin-4-one were added 20 ml of diethyl ether, 5 ml of water, 840 mg of sodium hydrogencarbonate, and 3.20 g of 2,4-dinitrobenzenesulfonyl chloride under ice-cooling, and the resulting mixture was stirred for 2 hours at the same temperature as above and then for 20 hours at room temperature. The reaction mixture obtained was concentrated under reduced pressure, and water and ethyl acetate were added to the residue formed to distribute the mixture between water and ethyl acetate. The organic layer was washed three times with water, dried with anhydrous magnesium sulfate, and concentrated again under reduced pressure. The residue formed was recrystallized from a mixture of ethanol and water to obtain 600 mg of 2-(2,4-dinitrobenzenesulfonohydrazono)thiazolidin-4-one as light yellow needle crystals. The melting point thereof was from 204° C. to 206° C.

By following the similar procedure to the above step, the following compound was obtained.

(2) 2-(4-Toluenesulfonohydrazono)thiazolydin-4-one

The melting point thereof was from 163° C. to 165° C.

(3) 2-(2,4-Dinitrobenzenesulfonohydrazono)imidazolidin-4-one

NMR (DMSO-d$_6$) $\delta$: 8.85 (s, 1H) 8.69 (d, J=8.58 Hz, 1H) 8.31 (d, J=8.58 Hz, 1H) 3.87 (s, 2H)

EXAMPLE 13

(1) A mixture of 514 mg of 3-ethoxycarbonylmethyl-2-isopropylidenehydrazonothiazolidin-4-one obtained in step (1) of Example 9, 197 mg of sodium acetate, 10 ml of acetic acid and 393 mg of terephthalaldehydric acid methyl ester was stirred for 3 hours at 80° C. The reaction mixture obtained was cooled, water was added thereto, and crystals thus precipitated were filtered and washed with water and diethyl ether to obtain 710 mg of 3-ethoxycarbonylmethyl-2-(4-methoxycarbonylbenzylidenehydrazono)thiazolidin-4-one.

(2) By following the similar hydrolysis reaction to step (2) of Example 2, 2-(4-carboxybenzylidenehydrazono)-3-carboxymethylthiazolidin-4-one was obtained.

NMR (DMSO-d$_6$) $\delta$ ppm: 8.52 (s, 1H) 7.71 to 8.12 (m, 4H) 4.41 (s, 2H) 4.09 (s, 2H)

By following the similar procedure to the above steps (1) and (2), the following compound was obtained.

(3) 3-Carboxymethyl-2-salicylidenehydrazonothiazolidin-4-one m.p. 258° to 263° C.

NMR (DMSO-d$_6$) $\delta$ ppm: 10.72 (s, 1H) 8.68 (s, 1H) 6.83 to 7.63 (m, 4H) 4.40 (s, 2H) 4.14 (s, 2H)

EXAMPLE 14

(1) By following the similar procedure to step (1) of Example 9, 3-cyclopentyl-2-isopropylidenehydrazonothiazolidin-4-one was obtained. The melting point thereof was 61° C. to 63° C.

By following the similar procedure to above, the following compounds were obtained.

(2) 2-Isopropylidenehydrazono-3-phenoxyacetylthiazolidin-4-one m.p. 172° to 175° C.

NMR (CDCl$_3$) δ ppm: 6.89 to 7.26 (m, 5H) 4.84 (s, 2H) 4.15 (s, 2H) 2.02 (s, 6H)

(3) 2-Isopropylidenehydrazono-3-methoxycarbonylphenoxyacetylthiazilidin-4-one

NMR (CDCl$_3$) δ ppm: 7.98 (d, J=8.35 Hz, 2H) 6.94 (d, J=8.35 Hz, 2H) 4.89 (s, 2H) 4.16 (s, 2H) 3.87 (s, 3H) 2.01 (s, 6H)

(4) 2-Isopropylidenehydrazono-1-methoxycarbonylmethyl-3-methylimidazolidin-4-one m.p. 90° to 92° C.

NMR (CDCl$_3$) δ ppm: 4.58 (s, 2H) 3.95 (s, 2H) 3.72 (s, 3H) 3.07 (s, 3H) 1.93 (d, J=2.64 Hz, 6H)

(5) 2-Isopropylidenehydrazono-3-methylimidazolidin-4-one

NMR (CDCl$_3$) δ ppm: 5.65 (br s, 1H) 3.97 (s, 2H) 3.11 (s, 3H) 2.02 (d, J=2.63 Hz, 6H)

(6) 2-Isopropylidenehydrazono-1,3-dimethylimidazolidin-4-one

NMR (CDCl$_3$) δ ppm: 3.83 (s, 2H) 3.37 (s, 3H) 3.05 (s, 3H) 1.99 (s, 6H)

EXAMPLE 15

(1) A mixture of 716 mg of 2-isopropylidenehydrazonothiazilidin-4-one synthesized by a known methol described in Can. J. Chem., 37, 1597–1607 (1959), 394 mg of sodium acetate, 10 ml of acetic acid, and 720 mg of terephthalaldehydric acid was stirred for 16 hours at 80° C. To the reaction mixture obtained were added water and chloroform to distribute the mixture between water and chloroform. The aqueous layer was further extracted three times with chloroform. The organic layer was combined with the extract, the mixture was dried over anhydrous magnesium sulfate and concentrated under reduced pressure. The residue formed was charged on silica gel column chromatography and eluted with a mixture of chloroform and methanol at 50:1 by volume ratio to obtain 1-(4-carboxybenzylidenehydrazono)thiazolidin-4-one having a melting point higher than 300° C.

NMR (DMSO-d$_6$) δ ppm: 8.46 (s, 1H) 7.77 to 8.12 (m, 4H) 3.91 (s, 2H)

By following the similar procedure to above, the following compounds were obtained.

(2) 2-(4-Carboxyphenoxyethylydenehydrazono)thiazolidin-4-one m.p. 255° to 260° C.

NMR (DMSO-d$_6$) δ ppm: 12.20 (brs, 1H) 7.83 to 7.93 (m, 3H) 7.06 (d, J=8.57 Hz, 2H) 4.86 (d, J=4.62 Hz, 2H) 3.85 (s, 2H)

(3) 2-(3,4,5-Trimethoxybenzylidenehydrazono)thiazolidin-4-one

NMR (DMSO-d$_6$) δ ppm: 11.87 (brs, 1H) 8.29 (s, 1H) 7.07 (s, 2H) 3.81 (s, 9H) 3.71 (s, 2H)

(4) 2-Phenylpropylidenehydrazonothiazolidin-4-one

NMR (DMSO-d$_6$) δ ppm: 11.69 (brs, 1H) 7.71 (t, J=5.1 Hz, 1H) 7.23 (s, 5H) 3.80 (s, 2H) 2.49 to 2.83 (m, 4H)

(5) 2-(2-Nitrocinnamylidenehydrazono)thiazolidin-4-one

NMR (DMSO-d$_6$) δ ppm: 7.0 to 8.25 (m, 7H) 3.81 (s, 2H)

EXAMPLE 16

By following the same procedure as step (1) of Example 4 but using 2-(2,4-dinitrobenzenesulfonohydrazono)-3-ethoxycarbonylmethylazolidin-4-one obtained in step (3) of Example 10, 5-cinnamylidene-2-(2,4-dinitrobenzenesulfonohydrazono)-3-ethoxycarbonylmethylthiazolidin-4-one was obtained.

NMR (CDCl$_3$) δ ppm: 8.68 (s, 1H) 8.55 (d, J=8.35 Hz, 1H) 8.27 (d, J=8.57 Hz, 1H) 6.63 to 7.60 (m, 8H) 4.41 (s, 2H) 4.15 (q, J=6.81 Hz, 2H) 1.23 (t, J=5.49 Hz, 3H)

By following the similar procedure to above, the following compound was obtained.

(2) 2-(2,4-Dinitrobenzenesulfonohydrazono)-3-ethoxycarbonylmethyl-5-(2-α-methylcinnamylidene)-thiazolidin-4-one NMR (CDCl$_3$) δ ppm: 8.69 (s, 1H) 8.55 (d, J=8.79 Hz, 1H) 8.28 (d, J=7.92 Hz, 1H) 6.80 to 7.59 (m, 7H) 4.42 (s, 2H) 4.15 (q, J=7.25 Hz, 2H) 2.30 (s, 3H) 1.23 (t, J=6.59 Hz, 3H)

Pharmacological Test 1

According to the following method, the in vitro effect of the compounds of the present invention and the comparative compounds for inhibiting the Maillard reaction was measured. That is, a bovine serum albumin having a concentration of 100 mg/ml, glucose having a concentration of 400 mM, and 5 mM of the test compound were dissolved in a buffer solution of 0.5M sodium phosphate having pH of 7.4, and the mixture was incubated for 2 weeks at 37° C. Of the test compounds used, each of the compounds of Example 1 (3), Example 2 (5), Example 5 (3) and (4), Example 6 (1), Example 9 (2), Example 10 (5), Example 12 (1), and Example 15 (1) was dissolved at a concentration of 6 mM and the incubation was carried out for 12 days at 37° C.

After completion of the incubation, the culture liquid was diluted 100 times with a phosphate-buffered saline solution containing 0.01% (w/v) Tween 80, and the fluorescence of the resulting solution was measured at an excited wavelength of 370 nm and a fluorescent wavelength of 440 nm.

The percent inhibition ratio was calculated by the following formula:

Inhibition ratio
(%)={[(A−B)−(C−D)]/(A−B)}×100 wherein,

A: Fluorescence of (bovine serum albumin+glucose)

B: Fluorescence of bovine serum albumin

C: Fluorescence of (bovine serum albumin+glucose+the test compound)

D: Fluorescence of (bovine serum albumin+the test compound)

The results are shown in Table 1 below.

TABLE 1

| Example No. | Inhibition Ratio (%) | Example No. | Inhibition Ratio (%) |
|---|---|---|---|
| 1 (1) | 91 | 3 (2) | 24 |
| 1 (2) | 10 | 3 (3) | 5 |
| 1 (3) | 26 | 3 (4) | 9 |
| 1 (4) | 10 | 4 (1) | 5 |
| 1 (5) | 27 | 4 (2) | 88 |
| 1 (6) | 13 | 5 (2) | 11 |
| 1 (7) | 4 | 5 (3) | 43 |
| 1 (8) | 7 | 5 (4) | 44 |
| 1 (9) | 8 | 5 (5) | 7 |
| 1 (10) | 18 | 5 (6) | 54 |
| 1 (11) | 39 | 5 (7) | 5 |
| 2 (1) | 2 | 6 (1) | 70 |
| 2 (2) | 4 | 7 (1) | 9 |
| 2 (3) | 25 | 7 (2) | 2 |
| 2 (4) | 6 | 8 (1) | 10 |
| 2 (5) | 46 | 8 (2) | 17 |
| 3 (1) | 49 | | |
| 9 (1) | 34 | 13 (1) | 12 |
| 9 (2) | 63 | 13 (2) | 33 |
| 9 (3) | 59 | 13 (3) | 41 |
| 9 (4) | 95 | 14 (1) | 27 |
| 9 (5) | 89 | 14 (2) | 5 |
| 10 (1) | 22 | 14 (3) | 10 |
| 10 (2) | 16 | 14 (4) | 3 |
| 10 (3) | 86 | 14 (5) | 82 |
| 10 (4) | 69 | 14 (6) | 33 |
| 10 (5) | 59 | 15 (1) | 67 |
| 10 (6) | 14 | 15 (2) | 43 |
| 10 (7) | 13 | 15 (3) | 24 |
| 10 (8) | 12 | 15 (4) | 10 |
| 11 (1) | 7 | 15 (5) | 43 |
| 11 (2) | 81 | 16 (1) | 89 |
| 11 (3) | 30 | 16 (2) | 95 |
| 12 (1) | 92 | Compound 1* | 61 |
| 12 (2) | 26 | Compound 2* | 73 |
| 12 (3) | 93 | Compound 3* | 41 |

*Test Compounds
Compound 1: 2-Hydrazonothiazolidin-4-one
Compound 2: 2-Isopropylidenehydrazonothiazolidin-4-one
Compound 3: 2-Hydrazonoimidazolidin-4-one Pharmacological Test 2

The compound of the present invention was tested in Streptozocin-induced diabetic rats in terms of urinary albumin excretion according to the procedure as described in T. Soulis-Liparota et al., Diabetes, Vol. 40, pp. 1328–1334, October, 1991, and D. Edelstein et al. Diabetologia (1992) 35:96–97.

Test Method

Streptozocin (STZ) was intravenously administered to fasted male SD rats weighing 170 g to 200 g at a dose of 50 mg/kg, and, after six days, rats showing a blood sugar level of 200 mg/dl or more were used for test. For the STZ-induced diabetic rats, the amount of albumin in the urine accumulated for 24 hours was determined by the ELISA (enzyme-linked immunosorbent assay). The rats were divided into two groups, and one groups (n=7) was administered with a physiological saline solution (containing 0.01% Polysorbate 80) of the test compound, 2-(2,4-dinitrobenzenesulfonohydrazono)-thiazolidin-4-one prepared in Example 12 (1) at a dose of 10 mg/kg, i.p., and the other group (n=7) was administered with the above-described solution but containing no test compound (Control). Also, non-treated male SD rats were used as a normal control group (n=6). The comparative study was conducted for 6 weeks while intraperitoneally administrating the solution once a day to the medicated group and the control group.

Test Results

The results obtained are shown in Figure. As is noted from the results in Figure, an inhibitory effect on the urinary albumin excretion was observed in the medicated group (-●- in Figure) after two week from the administration of the test compound. Thereafter, this effect lasted until the end of the test period of 6 weeks and, finally, a 54% inhibitory effect on urinary albumin excretion was observed as compared with that of the control group (-- in Figure).

PREPARATION EXAMPLE

The following components were mixed in a usual manner, and the resulting mixture was compressed by a tabletting machine into 100 tablets each containing 50 mg of the active ingredient.

| | |
|---|---|
| Compound of Example 10 (3) | 5 g |
| Sodium Laurylsulfate | 0.2 g |
| Magnesium Stearate | 0.2 g |
| Crystal Cellulose | 4.6 g |

While the invention has been described in detail and with reference to specific embodiments thereof, it will be apparent to one skilled in the art that various changes and modifications can be made therein without departing from the spirit and scope thereof.

What is claimed is:

1. A compound represented by formula (1)

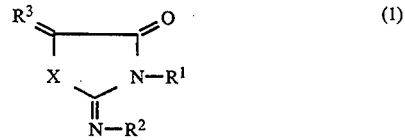

or a salt thereof, wherein $R^1$ is selected from the group consisting of a hydrogen atom, a lower alkyl group, a carboxyl lower alkyl group, and a lower alkoxy-carbonyl lower alkyl group; $R^2$ is $-N=R^6$, wherein $R^6$ is selected from the group consisting of a lower alkylidene group, a lower alkylidene group substituted with 1 or 2 lower cycloalkyl groups, a phenyl lower alkylidene group which may be substituted with a carboxy group on the phenyl ring thereof, a phenyl lower alkenylidene group, a lower alkenylidene group and a lower cycloalkylidene group; $R^3$ is two hydrogen atoms or a phenyl lower alkenylidene group; and X is $-N(R^7)-$, wherein $R^7$ is selected from the group consisting of a hydrogen atom, a lower alkyl group, a carboxy lower alkyl group and a lower alkoxy-carbonyl lower alkyl group; with the proviso that when $R^1$ is a hydrogen atom, $R^2$ is $-N=R^6$, and X is $-NH$, then $R^3$ and $R^6$ are not simultaneously a phenyl lower alkylidene group.

2. The compound or salt thereof as claimed in claim 1, wherein $R^1$ is a hydrogen atom, $R^3$ is two hydrogen atoms, and $R^6$ is a lower alkylidene group.

3. The compound or the salt thereof as claimed in claim 2, wherein $R^7$ is a hydrogen atom.

4. The compound or salt thereof as claimed in claim 3, wherein said compound is 2-isopropylidenehydrazonoimidazolidin-4-one.

5. A method for inhibiting a Maillard reaction in a living body, which comprises administering to a living body, a Maillard reaction inhibiting effective amount of a compound represented by formula (1');

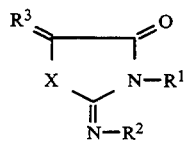 (1')

or a salt thereof, wherein $R^1$ is selected from the group consisting of a hydrogen atom, a lower alkyl group, a carboxy lower alkyl group, a lower alkoxy-carbonyl lower alkyl group, a phenoxy lower alkanoyl group which may be substituted with a lower alkoxycarbonyl group on the phenyl ring and a lower cycloalkyl group; $R^2$ represents —$NHR^4$ or —$N$=$R^6$, wherein $R^4$ is selected from the group consisting of a hydrogen atom, a phenyl-sulfonyl group which may be substituted with from 1 to 3 substituents selected from the group consisting of a halogen atom, a nitro group, a lower alkoxy group and a lower alkyl group on the phenyl ring thereof, a phenyl lower alkanoyl group and —CO—$NHR^5$, wherein $R^5$ is selected from the group consisting of a lower alkyl group, a phenyl group which may be substituted with a halogen atom on the phenyl ring thereof, a phenyl lower alkyl group and a naphthyl group, wherein $R^6$ is selected from the group consisting of a lower alkylidene group, a lower alkylidene group substituted with 1 or 2 lower cycloalkyl groups, a phenyl lower alkylidene group which may be substituted with from 1 to 3 substituents selected from the group consisting of a halogen atom, a carboxy group, a lower alkoxycarbonyl group, a nitro group, a hydroxy group, a lower alkoxy group, a halogenated lower alkyl group on the phenyl ring thereof, a phenyl lower alkenylidene group which may have a nitro group on the phenyl ring thereof, a lower alkenylidene group, a lower cycloalkylidene group and a phenoxy lower alkylidene group which may be substituted with a carboxy group on the phenyl ring thereof; $R^3$ is selected from the group consisting of two hydrogen atoms, a phenyl lower alkylidene group which may be substituted with a halogen atom or a halogenated lower alkyl group on the phenyl ring thereof and a phenyl lower alkenylidene group; and X represents —$N(R^7)$—, wherein $R^7$ is selected from the group consisting of a hydrogen atom, a lower alkyl group, a carboxy lower alkyl group and a lower alkoxycarbonyl lower alkyl group; and $R^1$ and $R^4$ or $R^4$ and $R^7$ may combine with each other to form an oxoethylene group.

6. The method for inhibiting a Maillard reaction in a living body as claimed in claim 4, wherein the method is employed to treat complications caused by diabetes.

* * * * *